United States Patent [19]

Namiki et al.

[11] Patent Number: 4,649,206

[45] Date of Patent: Mar. 10, 1987

[54] LIGNAN COMPOUND

[75] Inventors: Mitsuo Namiki, Nagoya; Toshihiko Osawa, Chiyodabashi; Yasuko Fukuda, Nagoya; Tatsuhiko Ozaki, Nishio, all of Japan

[73] Assignee: Takemoto Yushi Kabushiki Kaisha, Aichi, Japan

[21] Appl. No.: 771,982

[22] Filed: Sep. 3, 1985

[51] Int. Cl.$^4$ ............................................. C07D 407/00
[52] U.S. Cl. ..................................... 549/435; 252/404
[58] Field of Search ........................................ 549/435

[56] References Cited

U.S. PATENT DOCUMENTS 2,837,534  6/1958  Tracy .................................. 549/435

Primary Examiner—Dolph H. Torrence
Attorney, Agent, or Firm—Flehr, Hohbach, Test, Albritton & Herbert

[57] ABSTRACT

This invention relates to a lignan compound having antioxidative characteristics, an antioxidant having this lignan compound as active component, and antioxidants having as active component a product which contains this lignan compound and is obtained by causing $\beta$-glucosidase to react with crushed sesame seeds or a solvent extract thereof.

2 Claims, 1 Drawing Figure

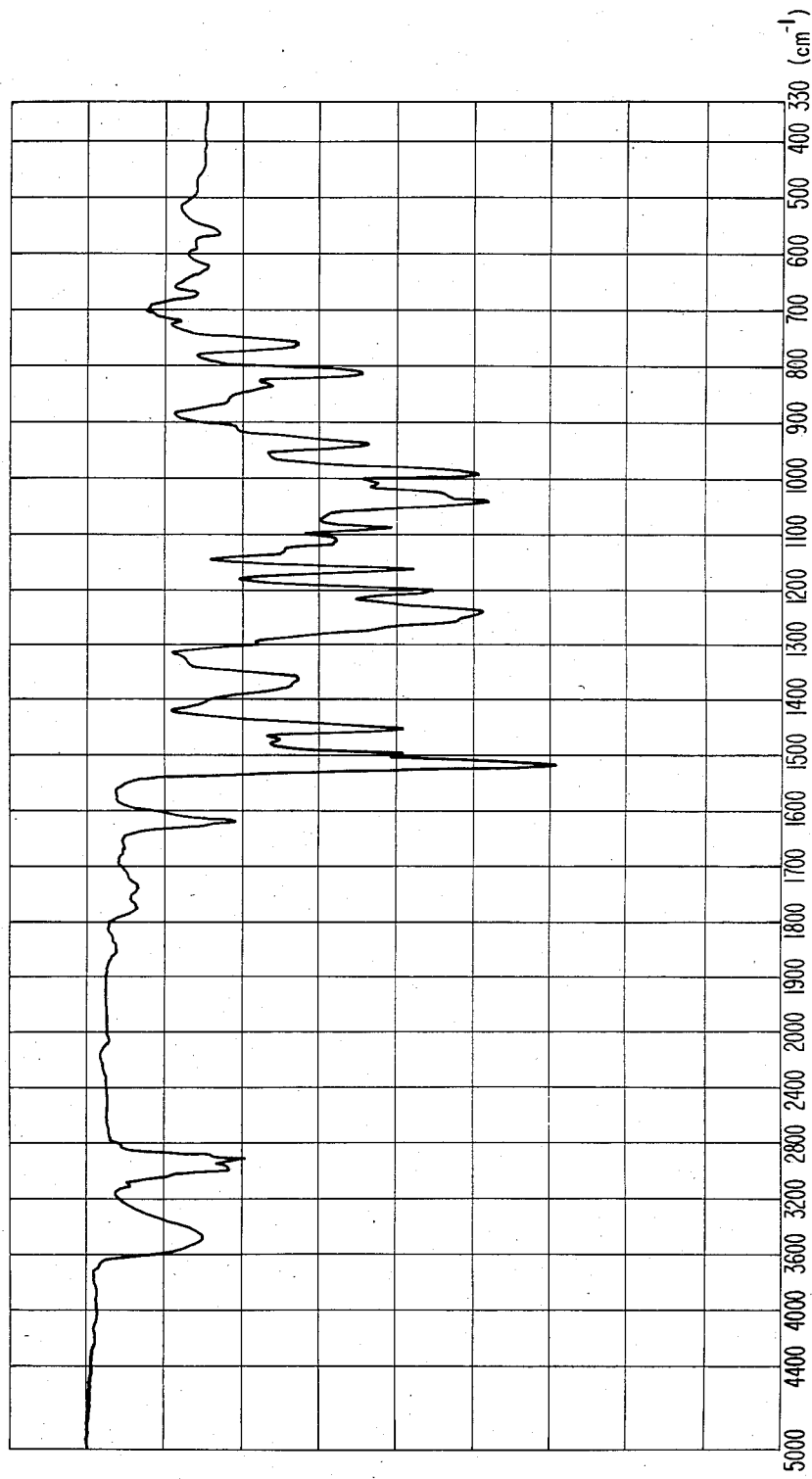
FIG.—I.

LIGNAN COMPOUND

This invention relates to a new lignan compound and antioxidants containing the same.

It is well known that edible oils and fats as well as processed foods containing them lose freshness and undergo degradation, etc. during processing and storage due to autoxidation of oils and fats. For this reason, it is generally the practice to take some measures to prevent such oxidative degradation in the case of animal or vegetable oils or fats such as bean oil, rape seed oil, sunflower seed oil, coconut oil, lard and fish oils or processed foods containing oils and fats such as dressings, shortenings, butter, margarine, ham, sausages, instant Chinese noodles and fried bakery products. Bleaching by the sunlight or artificial light beams, on the other hand, is also observed on pigments and coloring matters such as carotin contained naturally in or added artificially to juices and carbonated drinks. In this situation, too, a measure must be taken somehow so that these foods can be preserved in an improved manner. It is already well known that such measures for preventing oxidative degradation are required not only relating to foods but in a wide range of industrial fields. Many types of antioxidants and preservatives have conventionally been used as food additives. Some of them are natural while some are artificial. Currently, rules and regulations are being imposed on their use from the point of view of safety and the public is beginning to become aware of the problems related to additives that may be used on foods. It is therefore very important to make safe additives available.

In view of the situation described above, the present inventors diligently researched for a safe and effective antioxidant and completed this invention by discovering that a new lignan compound is produced by the reaction of a component contained in sesame seeds with β-glucosidase and that not only this lignan compound itself but also certain compound products which contain this lignan compound exhibit superior antioxidative characteristics.

In other words, the present invention relates firstly to a lignan compound shown by the formula (I) below, secondly to an antioxidant having the aforementioned lignan compound as its active component, and thirdly to antioxidant having as its active component a product which contains the aforementioned lignan compound and is obtained by causing β-glucosidase to react with crushed sesame seeds or a solvent extract thereof:

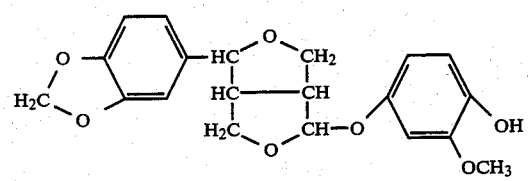

(I)

As will be described in detail below, the lignan compound shown by the formula (I) (hereinafter to be referred to as the compound of this invention) is produced by a reaction between a component contained in sesame seeds and β-glucosidase. Although it is similar to sesamolin which has the structure shown by the formula (II) below and has long been known as a peculiar substance contained in sesame seeds, it is a completely new compound, having a different chemical structure:

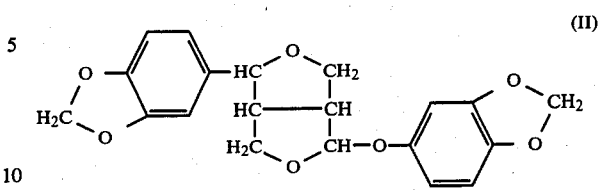

(II)

The compound of this invention is effective as an antioxidant, exhibiting prominent antioxidative characteristics, as will be described below in detail. By contrast, aforementioned sesamolin does not show any antioxidative property. While synthetic substances such as butylhydroxytoluene (BHT) and butylhydroxyanisole (BHA), which have conventionally been used as antioxidants for preventing oxidation of oil- and fat-containing foods and coloring matters, are currently being criticized and avoided for their toxic and carcinogenic properties, the antioxidants having the compound of this invention as active component are precisely the answer to the society's wish for an effective and safe antioxidant.

The compound of this invention can be produced also by the reaction of microorganisms such as Bacillus natto and Rhizopus oligosporus on sesame seeds but it can be produced advantageously by causing β-glucosidase to react with crushed sesame seeds or a solvent extract thereof.

As crushed sesame seeds, use may be made of de-oiled sesame seeds after oil has been squeezed out. There are many methods of separating sesame seeds into sesame seed oil and de-oiled sesame seeds. Oil is generally squeezed out mechanically at a high pressure either directly from sesame seeds or after the seeds are roasted. In certain situations, hexane and the like may be used on de-oiled sesame seeds for further extraction. Accordingly to the present invention, it does not matter whether sesame seeds are roasted or not, nor whether or not a solvent is used for extraction. All forms of de-oiled sesame seeds can be used for the present invention. Although sesame seeds before de-oiling can also be used by the present invention, it is necessary to compress sesame seeds in this situation in order to improve the efficiency of subsequent processing. From the point of view of the objects of the present invention, however, it is preferable to use de-oiled sesame seeds in order to reduce the content of unnecessary oil and fat components.

Another raw material to be considered for the present invention is the extracts from aforementioned crushed sesame seeds by water, an organic solvent or a mixed solvent. Suitable as organic solvents are such polar solvents as methanol, ethanol, propanol and isopropanol. In particular, extracts obtained with an aqueous alcohol with weight ratio between methanol, ethanol, propanol, isopropanol or their mixture and water in the range of 10:90 to 90:10 are preferable because the extraction efficiency of substances useful to the present invention is high, the content of substances useless to the present invention is low and they are suited for the subsequent process involving reaction with β-flucosidase. When an organic solvent is used for extraction, the extracts should be dried or condensed until there remains no organic solvent so that β-glucosidase will not undergo oxidative degradation in a later process.

The processing by β-glucosidase is carried out under the condition where crushed sesame seeds or a solvent extract thereof is dispersed or dissolved in water. A preliminary sterilization process is desirable in this situation in order to present contamination by harmful microorganisms. Methods by heating and use of sterilizing filters are available but these methods do not limit the present invention. In order to make β-glucosidase to effectively react, it is desirable to adjust the pH value, etc. by temperature or a buffer solution. In general, a pH value in the range between 3 and 7 is preferable at temperature 30°-60° C.

After the processing with β-glucosidase as described above, a solvent such as ethyl acetate and n-butyl alcohol which has a high solubility against polar substances such as saccharide, protein, peptide and amino acids but can dissolve phenols, is used for extraction. The compound of this invention is obtained by a chromotographic method with a substance like silica gel used as a fixed phase. As an example, when Kieselgel 60F254 of TLC plate by Merck Corporation was used and n-hexane/ethyl acetate=3/2(V/V) was used to develop, the compound of this invention was obtained from the section $R_f=0.41$. If the processing by β-glucosidase or microorganisms like Bacillus natto and Rhizopus oligosporus is omitted, the compound of this invention cannot be detected from the extract from the unprocessed raw material.

Structure of the compound of this invention thus obtained has been examined as follows. First, it was ascertained by double focussing mass spectrum analysis that its molecular weight is 372.12 and that its molecular formula is $C_{20}H_{20}O_7$. It was then determined from mass spectrum and $^{13}C$-NMR methods that it has the structure of sesamolin with one of methylenedioxy groups opened. Details will be discussed below by examples.

As explained above, the compound of this invention with superior antioxidative capability can be effectively produced by processing crushed sesame seeds or a solvent extract thereof with β-glucosidase. The product obtained by the aforementioned process, however, contains not only the compound of this invention but also other compounds which, too, exhibit superior antioxidative properties. Thus, the compound product obtained by the aforementioned process is also found to be an excellent antioxidant. Such compound product can be obtained effectively as follows.

When crushed sesame seeds are used, either a solvent with a low solubility in water such as ethyl acetate or butanol is used to extract the antioxidant components or a water-soluble solvent such as methanol, ethanol, propanol or isopropanol is added and the residue is separated by filtering or by using an centrifugal separator after the processing with β-glucosidase. The solution thus obtained is processed as will be explained for the case where a solvent extract is used.

When a solvent extract of crushed sesame seeds is used, a solvent with low solubility in water such as ethyl acetate or butanol is used to extract the antioxidant component or the product is directly dried subsequent to the processing with β-glucosidase. Alternatively, a water-soluble solvent such as methanol, ethanol, propanol, isopropanol, a mixture thereof, or an aqueous solution thereof or a solvent with low solubility in water such as ethyl acetate or butanol may be used for re-extraction after drying or condensation. In addition to the aforementioned compound of this invention shown by the formula (I), the following compounds shown by the formulas (III) and (IV) have also been identified as antioxidant components in the product thus obtained:

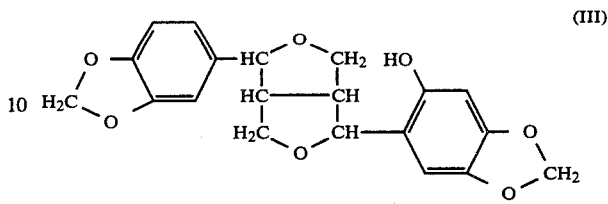

(III)

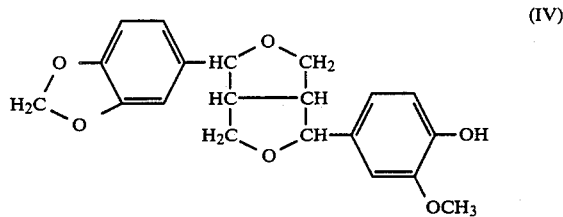

(IV)

The compounds shown by the formulas (I), (III) and (IV) have molecular structures which may resemble but are quite different from those of sesamolin shown by the formula (II) above and sesamin shown below by the formula (V) both of which have long been known as peculiar substances contained in sesame seeds. They are all strongly antioxidant while neither sesamolin nor sesamin exhibit antioxidative characteristics:

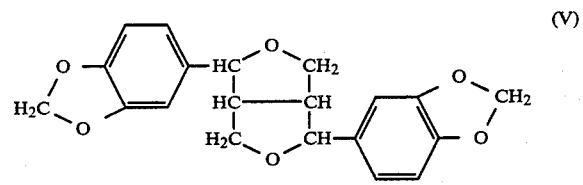

(V)

By name, the compound shown by the formula (I) is tetrahydro-1-[3-methoxy-4-hydroxyphenoxy]-4-[3,4-(methylenedioxy)phenyl]-1H,3H-furo[3,4-C]furan, the compound shown by the formula (III) is tetrahydro-1-[6-hydroxy-3,4-(methylenedioxy)phenyl]-4-[3,4-(methylenedioxy)phenyl]-1H,3H-furo[3,4-C]furan, and the compound shown by the formula (IV) is tetrahydro-1-[3-methoxy-4-hydroxyphenyl]-4-[3,4-(methylenedioxy)phenyl]-1H,3H-furo[3,4-C]furan.

In what follows, there will be presented further details of this invention and its effects by way of examples and experimental results.

EXAMPLE 1

An expeller was used to press sesame seeds produced in China to squeeze out oil components and 45 kg of 76% (W/W) ethanol was added to 10 kg of the de-oiled sesame seeds (with 8.9% of residual oil component). After this mixture was stirred for 10 hours at room temperature, 37 kg of extract solution was obtained by filtering. When this filtered extract solution was condensed to 4.2 kg by using a flush evaporator at liquid temperature below 40° C., the solid component was 11.4%. After 150 g of active charcoal was added and the mixture was stirred for one hour at room temperature, it was filtered and condensed by an evaporator to obtain 789 g of condensed liquid with 54% of solid component.

To 700 g of this condensed liquid was added an enzyme solution with 2.8 g of β-glucosidase (5000 U/g) by Sigma Corporation dissolved in 560 g of M/10 acetic acid-sodium acetate buffer and also 1500 g of the same buffer. The mixture was stirred for 24 hours at 37° C. for hydrolysis of the extract. Thereafter, extraction from this processed liquid was carried out three times by using 5000 ml of ethyl acetate. The ethyl acetate layer was dehydrated overnight with anhydrous sodium sulfate and 54 g of yellowish brown solid was obtained by filtering the removing the solvent.

This solid object was sequentially developed by using a column (silica gel 370 g, inner diameter of column 32 mm, height of silica gel layer 1200 mm) of silica gel (BW-820H by Fuji-Davidson Chemical Company) with 600 ml each of n-hexane, n-hexane/ethyl acetate=9/1, 8/2, 7/3, 6/4, 5/5, 4/6, 3/7, 2/8 and 1/9, and ethyl acetate. A 262 mg-portion eluting in the range of n-hexane/ethyl acetate=5/5-4/6 was obtained. Use was further made of Kieselgel 60F254 of TLC plate by Merck Corporation to develop with n-hexane/ethyl acetate=3/2 (V/V) to obtain a substance with $R_f$=0.41. At the end, 82 mg of a colorless solid (the compound of this invention) was obtained.

Results of analysis on this separated substance are shown below:

Double focussing MS (relative intensity is shown inside parentheses): 372.1234 ($M^+$, 40), 250.0955 (59), 233.0856 (38), 203.0775 (61), 194.0841 (12), 176.0492 (22), 152.0495 (22), 150.039 (121), 140.0514 (89), 136.0568 (31), 135.0480 (210).

$^{13}$C-NMR (solvent CDCl$_3$, $\delta_c$): 52.7 (d), 53.2 (d), 55.8 (q), 69.6 (t), 71.1 (t), 86.8 (d), 100.9 (t), 101.4 (d), 106.3 (d), 106.6 (d), 108.0 (d), 108.6 (d), 114.0 (d), 119.4 (d), 134.1 (s), 140.5 (s), 146.6 (s), 147.0 (s), 147.7 (s), 150.1 (s).

IR (by thin film method with NaCl plate): See FIG. 1.

UV (with 95% ethanol solution, absorption extremely large, nm): 287,231.

In addition, 89 g of the aforementioned condensed liquid with 54% solid component was diluted with 200 g of 0.1M acetic acid-sodium acetate buffer with pH 5 and extraction was carried out three times with 100 ml of ethyl acetate. The extraction was dehydrated and dried, resulting in 120 mg of substance soluble in ethyl acetate but the spot at $R_f$=0.41 was not observed when this was developed by using Kieselgel 60F254 of TLC plate by Merck Corporation with n-hexane/ethyl acetate=3/2 (V/V).

Test No. 1

The antioxidative characteristics of the compound of this invention were tested as follows by the rhodonite method. Samples of 0.2 mg each of sesamin, sesamolin and the compound of this invention (and also 0.4 mg of the compound of this invention) were individually added to 0.13 ml of linoleic acid purified by distillation, 10 ml of 99% ethanol and 10 ml of 0.1M NaOH-KH$_2$PO$_4$ buffer in a 50 ml triangular flask with a plug. Distilled water was further added to it to make a 25 ml solution. The flask was plugged and placed inside a heat reservoir at 40° C. and the progress in oxidation of linoleic acid was observed by periodically extracting 0.2 ml of the sample solution into an 18.5 cm test tube. Exactly three minutes after 9.4 ml of 75% ethanol, 0.2 ml of 30% water solution of ammonium thiocyanate, and 0.2 ml of 3.5% hydrochloric acid solution of 0.02M ferrous chloride were added, light absorption was measured at 500 nm to determine the color emission caused by peroxides. The result is shown in Table 1 which prominently exhibits antioxidative characteristics of the compound of this invention while no antioxidative characteristics are observable with sesamin and sesamolin

TABLE 1

| Sample | Added Amount (mg) | Light Absorptivity | | | | | |
|---|---|---|---|---|---|---|---|
| | | Right After | 2 days | 5 days | 7 days | 10 days | 15 days |
| None (control) | — | .025 | .561 | 1.0< | | | |
| Sesamin | 0.2 | .025 | .560 | 1.0< | | | |
| Sesamolin | 0.2 | .025 | .552 | 1.0< | | | |
| Compound of this invention | 0.2 | .025 | .111 | .320 | .590 | 1.0< | |
| Compound of this invention | 0.4 | .025 | .070 | .162 | .229 | .345 | .671 |

EXAMPLE 2

An expeller was used to press sesame seeds produced in China to squeeze oil components and 45 kg of 70% (W/W) ethanol was added to 1 kg of the de-oiled sesame seeds (with 8.8% of residual oil) in a 10 l flask with four openings. After the mixture was stirred for 10 hours at room temperature, 3.8 kg of extract solution was obtained by filtering. When this filtered extract solution was condensed to 450 g by using an evaporator at less than 40° C., the solid component was 11.6%. After 15 g of active charcoal was added to it and the mixture was stirred for one hour at room temperature, it was filtered and condensed by an evaporator at less than 40° C. to obtain 122 g of condensed liquid with 36% of solid component.

To 60 g of this condensed liquid was added an enzyme solution with 100 mg of β-glucosidase (5000 U/g) of Sigma Corporation dissolved in 40 g of M/10 acetic acid-sodium acetate buffer and also 100 g of the same buffer. The mixture was stirred for 24 hours at 37° C. Thereafter, extraction from this processed liquid was carried out three times by using 200 ml of ethyl acetate. The ethyl acetate layer was dehydrated overnight with anhydrous sodium sulfate and 430 mg of yellowish brown solid (to be called A) was obtained by filtering and removing the solvent.

Separately, 140 g of an acetic acid-sodium acetate buffer with pH 5 was added to 60 g of the aforementioned condensed liquid with 36% of solid and extraction was carried out three times with 200 ml of ethyl acetate. The ethyl acetate layer was dehydrated overnight with anhydrous sodium sulfate, filtered and dried, and 61 mg of yellowish brown solid (to be called B) was obtained.

EXAMPLE 3

After sesame seeds produced in China were crushed, their oil was extracted by n-hexane and 50 g of de-oiled sesame seeds (with 0.81% of residual oil component) were taken inside a triangular 1 l flask. After 400 g of distilled water was added, it was sterilized in an autoclave for 20 minutes at 120° C. After this was cooled down to room temperature, its measured pH value was 5.92. An enzyme solution with 100 mg of β-glucosidase (5000 U/g) by Sigma Corporation dissolved in 100 g of M/10 acetic acid-sodium acetate buffer at pH 5 was added to it and the mixture was stirred for 24 hours at 38° C. Thereafter, the contents were filtered and 246 g of filtered solution was obtained. Extraction was carried out three times therefrom by using 200 ml of ethyl acetate. After the ethyl acetate layer was dehydrated overnight with anhydrous sodium sulfate, it was filtered and 97 mg of a mixture of yellowish brown oil-like and solid substances (to be called C) was obtained by filtering and removing the solvent.

Test No. 2

After 20 mg each of the three types of extracts A, B and C obtained by Examples 2 and 3 as well as 40 mg of commercially available bean lecithin were individually dissolved uniformly in 2 ml of chloroform, the solvent was removed therefrom to produce mixtures of the individual extracts and lecithin. Thereafter, 12 mg each of these mixtures, 8 mg of lecithin, 4 mg dl-α-tocopherol, and 40 mg of a commercially available natural oxidant (SP-10 by Lion McCormick) were individually taken into 100 ml triangular flasks, into which 20 g each of refined sesame oil purified through a base alumina column was added. They were heated to 50° C. and shaken thoroughly to dissolve the contents. They were kept inside an oven at 98° C. and the amount of peroxides (meq/kg) was measured over a period of time. The results are shown in Table 2. Table 2 demonstrates clearly that the extracts A and C of the present invention exhibit superior antioxidative characteristics.

TABLE 2

| Antioxidant | Added Amount (mg) | Peroxide | | | | |
|---|---|---|---|---|---|---|
| | | 0 hrs | 3 hrs | 5 hrs | 7 hrs | 10 hrs |
| A + Lecithin | 4 + 8 | 6.5 | 26 | 38 | 74 | 125 |

TABLE 2-continued

| Antioxidant | Added Amount (mg) | Peroxide | | | | |
|---|---|---|---|---|---|---|
| | | 0 hrs | 3 hrs | 5 hrs | 7 hrs | 10 hrs |
| C + Lecithin | 4 + 8 | 6.5 | 41 | 68 | 102 | 187 |
| B + Lecithin | 4 + 8 | 6.5 | 52 | 92 | 136 | 200< |
| Lecithin | 8 | 6.5 | 58 | 100 | 143 | 200< |
| dl-α-tocopherol | 4 | 6.5 | 22 | 30 | 53 | 138 |
| Natural antioxidant | 40 | 6.5 | 62 | 106 | 137 | 200< |
| None (control) | — | 6.5 | 72 | 120 | 168 | 200< |

What is claimed is:

1. A lignan compound shown by the formula

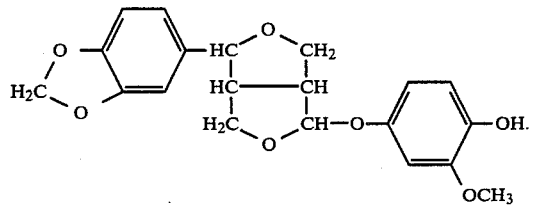

2. A method of producing an antioxidant having as active component a lignan compound shown by the formula

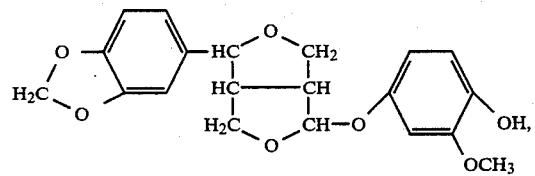

comprising the step of causing β-glucosidase to react with crushed sesame seeds or a solvent extract thereof.

* * * * *